United States Patent
Kondo et al.

(10) Patent No.: US 11,762,106 B2
(45) Date of Patent: Sep. 19, 2023

(54) SCINTILLATOR ARRAY, METHOD FOR MANUFACTURING SCINTILLATOR ARRAY, RADIATION DETECTOR, AND RADIATION INSPECTION DEVICE

(71) Applicants: KABUSHIKI KAISHA TOSHIBA, Tokyo (JP); TOSHIBA MATERIALS CO., LTD., Yokohama (JP)

(72) Inventors: Hiroyasu Kondo, Yokohama (JP); Kazumitsu Morimoto, Yokohama (JP)

(73) Assignees: KABUSHIKI KAISHA TOSHIBA, Tokyo (JP); TOSHIBA MATERIALS CO., LTD., Yokohama (JP)

( * ) Notice: Subject to any disclaimer, the term of this patent is extended or adjusted under 35 U.S.C. 154(b) by 0 days.

(21) Appl. No.: 17/660,658

(22) Filed: Apr. 26, 2022

(65) Prior Publication Data

US 2022/0252739 A1 Aug. 11, 2022

Related U.S. Application Data

(63) Continuation of application No. PCT/JP2020/040814, filed on Oct. 30, 2020.

(30) Foreign Application Priority Data

Oct. 31, 2019 (JP) .................. 2019-198878

(51) Int. Cl.
| | | |
|---|---|---|
| *G01T 1/20* | (2006.01) | |
| *A61B 6/00* | (2006.01) | |
| *C09K 11/02* | (2006.01) | |
| *C09K 11/77* | (2006.01) | |
| *A61B 6/03* | (2006.01) | |
| *G01N 23/046* | (2018.01) | |

(52) U.S. Cl.
CPC .............. *G01T 1/20* (2013.01); *A61B 6/4216* (2013.01); *C09K 11/02* (2013.01);
(Continued)

(58) Field of Classification Search
CPC ......... G01T 1/20; G01T 1/2002; G01T 1/202; A61B 6/4216; A61B 6/035; A61B 6/032;
(Continued)

(56) References Cited

U.S. PATENT DOCUMENTS

| 5,179,284 A * | 1/1993 | Kingsley ................. B29C 51/16 |
|---|---|---|
| | | 257/E31.118 |
| 5,208,460 A * | 5/1993 | Rougeot .................. G01T 1/202 |
| | | 250/366 |

(Continued)

FOREIGN PATENT DOCUMENTS

| JP | 2007-147581 A | 6/2007 |
|---|---|---|
| JP | 2014-048270 A | 3/2014 |

(Continued)

OTHER PUBLICATIONS

International Search Report and Written Opinion (Application No. PCT/JP2020/040814) dated Jan. 19, 2021 (with English translation).

*Primary Examiner* — Kiho Kim
(74) *Attorney, Agent, or Firm* — BURR PATENT LAW, PLLC (57) ABSTRACT

A scintillator array includes: a structure having at least one scintillator segment and a first reflective layer, the at least one scintillator segment and the first reflective layer having a first surface and a second surface, the at least one scintillator segment having a sintered compact containing a rare earth oxysulfide phosphor, and the first reflective layer being configured to reflect light; and a second reflective layer provided above the first surface via an adhesive layer, the adhesive layer having a thickness of 2 μm or more and 40 μm or less, and the second reflective layer having a film configured to reflect light.

10 Claims, 3 Drawing Sheets

(52) U.S. Cl.
CPC ........... *C09K 11/7771* (2013.01); *A61B 6/035* (2013.01); *G01N 23/046* (2013.01)

(58) Field of Classification Search
CPC ..... A61B 6/4233; A61B 6/4266; C09K 11/02; C09K 11/7771; G01N 23/046; G01N 2223/505; G21K 4/00; G21K 2004/04; H01L 27/14663
See application file for complete search history.

(56) References Cited

U.S. PATENT DOCUMENTS

| | | | |
|---|---|---|---|
| 6,452,186 B1* | 9/2002 | Wieczorek | G01T 1/2018 250/370.11 |
| 2006/0151706 A1 | 7/2006 | Minagawa et al. | |
| 2006/0233299 A1* | 10/2006 | Hoffman | G01N 23/046 378/19 |
| 2008/0290285 A1* | 11/2008 | Wakamatsu | G01T 1/2002 250/370.11 |
| 2014/0093041 A1 | 4/2014 | Takei et al. | |
| 2014/0301527 A1 | 10/2014 | Morimoto et al. | |
| 2015/0185337 A1 | 7/2015 | Kawanishi et al. | |
| 2018/0188386 A1 | 7/2018 | Kondo et al. | |
| 2018/0188387 A1 | 7/2018 | Morimoto et al. | |

FOREIGN PATENT DOCUMENTS

| | | |
|---|---|---|
| JP | 2014-071031 A | 4/2014 |
| JP | 2017-015627 A | 1/2017 |
| JP | 2018-044944 A | 3/2018 |
| WO | 2013/080565 A1 | 6/2013 |
| WO | 2017/082337 A1 | 5/2017 |
| WO | 2017/110850 A1 | 6/2017 |

* cited by examiner

SCINTILLATOR ARRAY, METHOD FOR MANUFACTURING SCINTILLATOR ARRAY, RADIATION DETECTOR, AND RADIATION INSPECTION DEVICE

CROSS-REFERENCE TO RELATED APPLICATIONS

This application is a continuation of prior International Application No. PCT/JP2020/040814 filed on Oct. 30, 2020; the entire contents of all of which are incorporated herein by reference.

FIELD

Embodiments described herein generally relate to a scintillator array, a method for manufacturing the scintillator array, a radiation detector, and a radiation inspection device.

BACKGROUND

A radiation inspection device such as an X-ray tomograph (hereinafter, referred to as an X-ray CT scanner) is used for inspection in various fields such as medical diagnosis and industrial nondestructive inspection. The X-ray CT scanner includes an X-ray tube (X-ray source) and an X-ray detector, the X-ray tube being capable of irradiating fan-beam X-rays, the X-ray detector having a plurality of X-ray detection elements, and the X-ray tube and the X-ray detector being disposed on the opposite side of a tomographic surface of an inspection target from each other.

The X-ray CT scanner irradiates fan-beam X-rays from the X-ray tube to the inspection target while rotating around the inspection target, and collects X-ray absorption data based on X-ray through the inspection target with the X-ray detector. Then, the X-ray absorption data is analyzed by a computer to form a tomogram.

A radiation detector in the X-ray CT scanner widely uses detection elements using a solid scintillator. The radiation detector having the detection elements with the solid scintillator can further increase resolution of the X-ray CT scanner and other devices because it is easy to downsize the detection elements and increase the number of channels.

The X-ray CT scanner and other radiation inspection devices are used in various fields such as medical and industrial applications. Examples of the X-ray CT scanner include a multi-slice device, which is formed by arranging the detection elements such as photodiodes on a two-dimensional array vertically and horizontally and then mounting a scintillator array onto the arranged detection elements. The multi-slice device can overlay computed tomography (CT) images to form a three dimensional CT image.

The radiation detector of the radiation inspection device includes a plurality of detection elements arranged in multiple vertical and horizontal rows, and each detection element has a scintillator segment. The radiation detector converts X-rays incident on the scintillator segments into visible light and converts the visible light into electrical signals by the detection elements to form an image. In recent years, the detection elements have been made smaller and a pitch between adjacent detection elements has been made narrower to obtain high resolution. These causes downsizing of the scintillator segment.

Among various scintillator materials used for the scintillator segment as described above, rare earth oxysulfide-based phosphor ceramics have high luminous efficiency and suitable characteristics for use in the scintillator segment. For this reason, radiation detectors combining scintillator segments each processed by cutting or grooving from a sintered compact (ingot) of rare earth oxysulfide-based phosphor ceramics, which are the scintillator materials, and photodiodes as the detection elements are becoming popular.

Examples of the scintillator using phosphor ceramics include a scintillator made of a sintered compact of a gadolinium oxysulfide phosphor. The scintillator array using the above scintillator is manufactured, for example, as follows. First, rare earth oxysulfide phosphor powder, which is the scintillator material, is molded into an appropriate shape and sintered to form a sintered compact (ingot). The sintered compact is then subjected to a cutting process such as cutting or grooving to form scintillator segments corresponding to a plurality of detection elements. Furthermore, a reflective layer that reflects light is formed between these scintillator segments and integrated to manufacture a scintillator array.

When the scintillator array is used in the radiation detector, dimensional accuracy of the scintillator array affects the resolution of CT diagnostic images. Furthermore, the radiation detector in the X-ray CT scanner is subjected to a temperature of 50° C. or more and 60° C. or less at most. The scintillator array with a reflective layer containing resin can expand the reflective layer due to temperature rise and shrink the reflective layer due to temperature drop, resulting in minute dimensional changes between adjacent scintillator segments, that is, variation or the like in external dimensions mainly due to pitch shift of the scintillator segments, and warpage of the scintillator array. These cause deterioration in the resolution of the diagnostic images produced by the radiation inspection device.

As the resolution of the diagnostic images using the radiation inspection device becomes higher and higher, there is a need for a scintillator array with less dimensional change due to heating and cooling. In addition, since an area of the scintillator array increases with the increase in a detection area of the radiation detector, it is important to control an amount of dimensional change due to heating and cooling.

DETAILED DESCRIPTION

A scintillator array according to an embodiment includes: a structure having at least one scintillator segment and a first reflective layer, the at least one scintillator segment and the first reflective layer having a first surface and a second surface, the at least one scintillator segment having a sintered compact containing a rare earth oxysulfide phosphor, and the first reflective layer being configured to reflect light; and a second reflective layer provided above the first surface via an adhesive layer, the adhesive layer having a thickness of 2 μm or more and 40 μm or less, and the second reflective layer having a film configured to reflect light.

Hereinafter, embodiments of the present invention will be explained with reference to the drawings. A relationship between a thickness and planar dimension of each component, a thickness ratio among the components illustrated in the drawings, and so on may be different from actual ones. Further, in the embodiments, substantially the same components are denoted by the same reference signs and a description thereof may be partly omitted.

A scintillator array, a radiation detector, and a radiation inspection device according to embodiments are described below.

(Scintillator Array)

Figure 1:
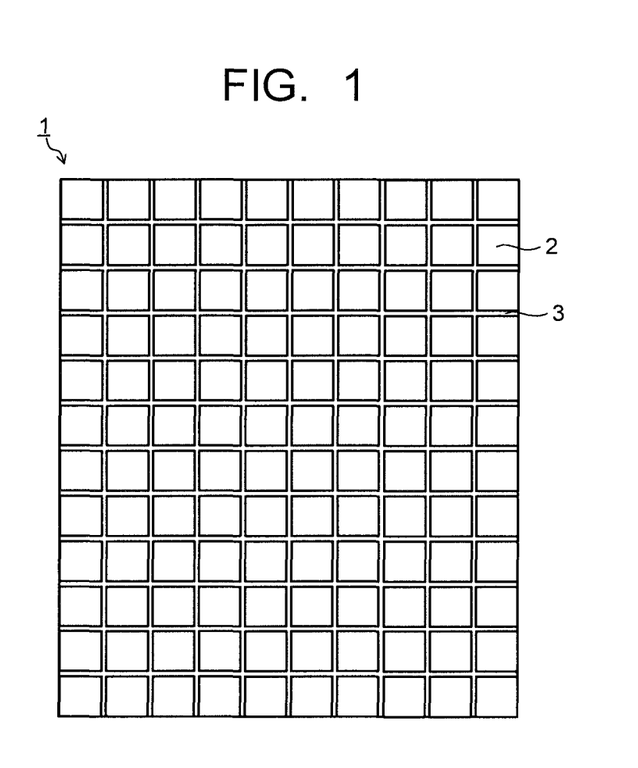
FIG. 1 is a plan view illustrating a structural example of a scintillator array.
Figure 2:
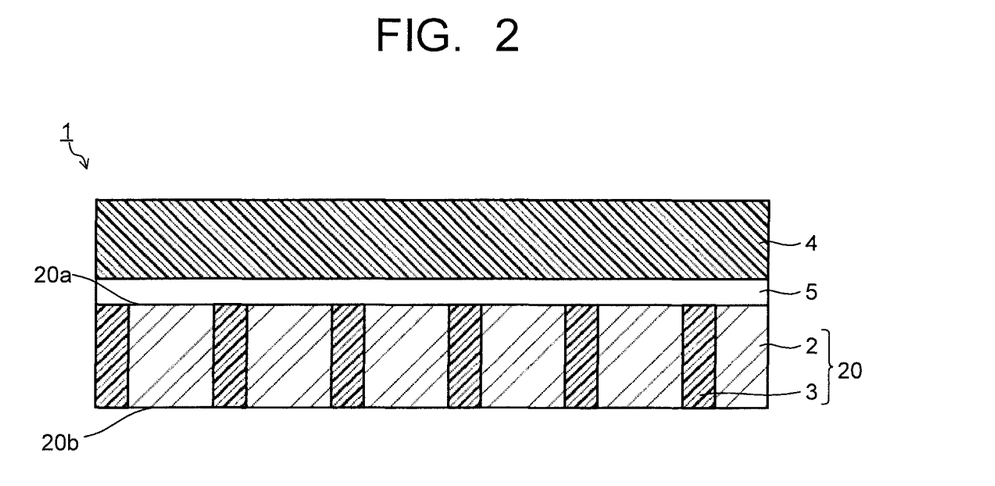
FIG. 2 is a cross-sectional view illustrating the structural example of the scintillator array.

FIG. 1 is a plan view illustrating a structural example of a scintillator array. FIG. 2 is a cross-sectional view illustrating the structural example of the scintillator array. FIG. 1 and FIG. 2 each illustrate a scintillator array 1, scintillator segments 2, a reflective layer 3, a reflective layer 4, and an adhesive layer 5. The reflective layer 4 and the adhesive layer 5 are omitted in FIG. 1 for convenience.

The scintillator array 1 includes scintillator segments 2, the reflective layer 3, the reflective layer 4, and the adhesive layer 5. The scintillator segments 2 and the reflective layer 3 form a structure 20 having a surface 20a, which is an X-ray incident surface, and a surface 20b on an opposite side of the surface 20a. The scintillator array 1 may have at least one scintillator segment 2. The number of scintillator segments 2 is set appropriately according to a structure, resolution, and the like of a radiation detector.

The scintillator segment 2 converts incident radiation rays (X-rays) into light (visible light). The scintillator segments 2 are integrated by the reflective layer 3 adhered thereto to form the structure 20.

The reflective layer 3 reflects light (visible light). The reflective layer 3 may transmit X-rays. The reflective layer 3 is provided between adjacent scintillator segments 2 and adheres to each scintillator segment 2.

The reflective layer 4 reflects light (visible light). The reflective layer 4 may transmit X-rays. As illustrated in FIG. 2, the reflective layer 4 is provided above the surface 20a via the adhesive layer 5 and covers the structure 20. The reflective layer 4 is formed by adhering a resin film, which is formed by molding a resin containing reflective particles that reflect light into a sheet form, to the surface 20a via the adhesive layer 5.

The scintillator array 1 may have either a structure where the scintillator segments 2 are arranged in a row or a structure where the scintillator segments 2 are arranged in a two-dimensional manner with the predetermined number of scintillator segments 2 in vertical and horizontal directions as illustrated in FIG. 1. When the scintillator segments 2 are two-dimensionally arranged, the reflective layer 3 is provided between the scintillator segments 2 arranged in the vertical direction and between the scintillator segments 2 arranged in the horizontal direction. The reflective layer 3 may surround the scintillator segments 2 along the surface 20a.

The scintillator segment 2 has a sintered compact containing a rare earth oxysulfide phosphor. Examples of the rare earth oxysulfide phosphor include the rare earth oxysulfide phosphor containing praseodymium (Pr) as an activator. Examples of rare earth oxysulfide include yttrium (Y), gadolinium (Gd), lanthanum (La), lutetium (Lu), and other oxysulfides of rare earth elements.

The rare earth oxysulfide phosphor preferably has a composition represented by:

general formula: $RE_2O_2S:Pr$     (1)

(in the formula, RE denotes at least one element selected from the group consisting of Y, Gd, La, and Lu)

Among the rare earth elements mentioned above, Gd, in particular, has a large X-ray absorption coefficient and contributes to improvement of light output of the scintillator array 1. Therefore, the scintillator segment 2 more preferably has a $Gd_2O_2S:Pr$ phosphor. Part of Gd may be substituted by other rare earth elements. At this time, a substitution amount of Gd by other rare earth elements is preferably 10 mol % or less.

That is, the rare earth oxysulfide phosphor preferably has a composition substantially represented by a general formula $(Gd_{1-x},RE_x)_2O_2S:Pr$     (2)

(in the formula, RE denotes at least one element selected from the group consisting of Y, La, and Lu, and x is a number (atomic ratio) satisfying $0 \leq x \leq 0.1$).

The scintillator segment 2 contains praseodymium (Pr) as the activator to increase the light output. Pr can reduce afterglow compared to other activators. Therefore, rare earth oxysulfide phosphor ceramics containing Pr as the activator is effective as a fluorescence generator for a radiation detector.

A content of Pr in the rare earth oxysulfide phosphor is preferably 0.001 mol % or more and 10 mol % or less of a content of a phosphor host (for example, $RE_2O_2S$ such as $Gd_2O_2S$). When the content of Pr is larger than 10 mol %, the light output may decrease. When the content of Pr is less than 0.001 mol %, an effect as a main activator cannot be sufficiently obtained. The content of Pr is more preferably 0.01 mol % or more and 1 mol % or less.

The rare earth oxysulfide phosphor may contain a small amount of at least one element selected from the group consisting of cerium (Ce), zirconium (Zr), and phosphorus (P) as a coactivator in addition to Pr as the main activator. These elements are effective in preventing exposure deterioration, afterglow, and the like. A total amount of these coactivators is preferably in a range of 0.00001 mol % or more and 0.1 mol % or less of the phosphor host.

A sintered compact constituting the scintillator segment 2 is preferably made of high-purity rare earth oxysulfide-based phosphor ceramics (scintillator material). Since impurities cause a decrease in sensitivity of the scintillator, it is preferable to reduce as much as possible the impurity amount. In particular, since a phosphate radical ($PO_4$) becomes the cause of the decrease in sensitivity, its content is preferably 100 ppm or less. In the case of using fluoride or the like as a sintering aid for densification of the sintered compact, the sintering aid remains as an impurity, causing the decrease in sensitivity.

The sintered compact has a cube shape or a rectangular parallelepiped shape. A volume of the scintillator segment 2 is preferably 1 $mm^3$ or less. Downsizing the scintillator segment 2 can form a detected image with higher definition. Each size of a length (L), breadth (S), and thickness (T) of the scintillator segment 2 does not be always limited but is preferably 1 mm or less. When the volume of the scintillator segment 2 is 1 $mm^3$ or less, a width (W) of the reflective layer 3 can be made thinner to 100 μm or less, and further to 50 μm or less.

The reflective layer 3 contains a resin that transmits light (light transmissive resin) and reflective particles that are dispersed in the resin and reflect light. The resin includes at least one selected from the group consisting of epoxy resin, silicone resin, phenol resin, urea resin, melamine resin, polyester resin, polyurethane resin, and acrylic resin. The reflective particles include at least one selected from the group consisting of titanium oxide, aluminum oxide (alumina), silicon oxide, barium sulfate, zinc oxide, zirconium oxide, and gadolinium oxide. Air bubbles contained in the resin may also have function as the reflective particles.

The reflective layer 4 can be made of the same light transmissive resin and reflective particles as the reflective layer 3. The reflective layer 4 is formed by processing a material containing the above light transmissive resin and reflective particles into a sheet form in advance to form a resin film, and then bonding the resin film to the surface 20a of the structure 20 via the adhesive layer 5. A commercially available white film can be used as the resin film.

A thickness of the reflective layer 4 is preferably 50 μm or more and 250 μm or less. When the thickness of the reflective layer 4 is less than 50 μm, an effect of improving reflection efficiency cannot be sufficiently obtained. When the thickness of the reflective layer 4 larger than 250 μm, a transmitted X-ray dose decreases and detection sensitivity decreases.

In the light transmissive resin constituting the reflective layer 3 and the reflective layer 4, a thermal expansion coefficient (linear expansion coefficient) at a temperature larger than the glass transition point is preferably $2\times10^{-5}/°$ C. or less. When the thermal expansion coefficient is larger than $2\times10^{-5}/°$ C., the changes (pitch shift of the scintillator segment 2, warpage and variation in external dimensions of the scintillator array 1) are likely to occur in finished dimensions of the scintillator array 1 due to the temperature during the manufacturing process of the X-ray CT scanner. The thermal expansion coefficient is further preferably $1.5\times10^{-5}/°$ C. or less.

To satisfy the glass transition point and thermal expansion coefficient, the light transmissive resin preferably has a molecular structure including a cyclo structure that includes no double structure (double bond). In the case where the molecular structure of the light transmissive resin includes the double structure, the glass transition point is likely to become less than 50° C.

The light transmissive resin constituting the reflective layer 3 and reflective layer 4 is preferably the epoxy resin having an aliphatic skeleton. Using the epoxy resin having the aliphatic skeleton makes it easier to enable the glass transition point and thermal expansion coefficient. Further, the epoxy resin as the light transmissive resin preferably has the molecular structure including the cyclo structure. Using such an epoxy resin makes it easier to increase the glass transition point and lower the thermal expansion coefficient at the temperature larger than the glass transition point.

Regarding a ratio between the light transmissive resin and the reflective particles in the reflective layer 3 and reflective layer 4, a mass ratio of the light transmissive resin is preferably 15% or more and 60% or less, and a mass ratio of the reflective particles is preferably 40% or more and 85% or less. The sum of the mass ratio of the light transmissive resin and the mass ratio of the reflective particles is 100%. When the mass ratio of the reflective particles is less than 40%, the reflection efficiency of the reflective layer decreases and the reflection efficiency of the reflective layer with respect to light having a wavelength of 512 nm is likely to be lower than 90%. When the mass ratio of the reflective particles is larger than 85%, the reflection efficiency of the reflective layer does not change, but the mass ratio of the light transmissive resin relatively decreases, resulting in difficulty in stable solidification of the reflective layer.

The adhesive layer 5 contains at least one resin selected from the group consisting of epoxy resin, silicone resin, acrylic resin, urethane resin, polyester resin, and polyolefin resin and cured by light, heat, or moisture. The adhesive layer 5 may be a light transmissive resin, but the adhesive layer 5 preferably contains at least one selected from the group consisting of titanium oxide, zirconium oxide, aluminum oxide, and silicon oxide to reduce that the light from one scintillator segment 2 enters the other one scintillator segment 2 through the adhesive layer 5.

Figure 3:
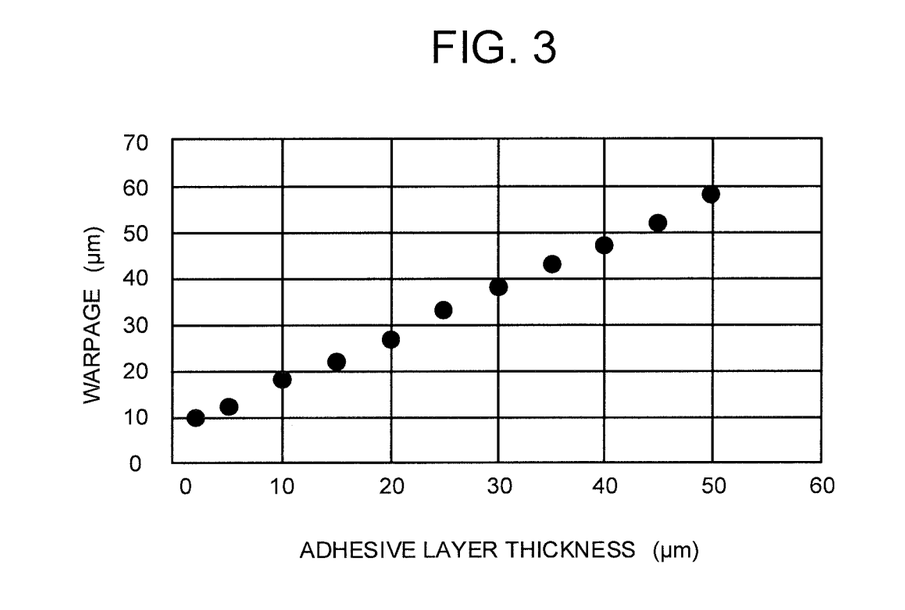
FIG. 3 is a view illustrating a relationship between an adhesive layer thickness and warpage of the scintillator array.

FIG. 3 is a view illustrating a relationship between a thickness of the adhesive layer 5 of the scintillator array 1 (adhesive layer thickness) and the warpage of the scintillator array 1. FIG. 3 illustrates a degree of improvement in the warpage of the scintillator array 1. An example of the scintillator array 1 is formed by integrating the scintillator segments 2 with a length (L), breadth (S), and thickness (T) all of size 1 mm with the reflective layer 3 of 100 μm in width to form the structure 20 of 76 mm in length and 25 mm in width, and then bonding a white polyethylene terephthalate (PET) film as the reflective layer 4 to the structure 20 by using the epoxy resin as the adhesive layer 5. FIG. 3 illustrates a variation of the warpage of the scintillator array 1 with the thickness of the adhesive layer 5.

The warpage of the scintillator array 1 is measured as follows. The warped scintillator array 1 usually has a convex surface and a concave surface. To measure the warpage, the scintillator array 1 is first placed on a flat surface with the convex surface down. The scintillator array 1 is away from an installation surface toward an end portion and rises upward. In this state, a vertical distance between a point where the scintillator array 1 rises the most and the installation surface is measured and is defined as the warpage. In general, the warpage of the scintillator array 1 is required to be 50 μm or less. No warpage means that a bottom surface of the scintillator array 1 is in contact with the installation surface at all points, and in this case, the warpage is 0 μm.

FIG. 3 shows that an increase of the thickness of the adhesive layer 5 increases the warpage. This is due to stress generated inside the adhesive layer 5 by shrinkage during a curing process. A value of the warpage has a range of approximately ±5 μm, but when the thickness of the adhesive layer 5 is larger than 50 the warpage also increases larger than 50 μm, which is not desirable. When the warpage is larger than 50 μm, pressurizing or polishing is usually required to correct the warpage, which makes the process more complicated.

The scintillator array 1 with a desirable warpage range can be formed by bonding a white film as the reflective layer 4 to the structure 20 via adhesive layer with an appropriate thickness, in a single process. This is thought to be because, for example, bonding a pre-formed flexible white film to the structure 20 via the relatively thin adhesive layer 5 reduces a volume of curing and shrinking, and thus the stress that causes warpage is less likely to occur in contrast to the conventional process where the reflective layer 4 is formed by thickly applying and curing.

The thickness of the adhesive layer 5 less than 2 μm likely weak adhesive strength to peel the reflective layer 4 from the structure 20. Therefore, the thickness of the adhesive layer 5 is preferably in a range of 2 μm or more and 40 μm or less, more preferably 5 μm or more and 30 μm or less. The thickness larger than 40 μm increases the volume of the cured and shrunk part of the adhesive layer 5 to increase the warpage of the scintillator array 1, which is not desirable.

The light transmissive adhesive layer 5 can transmit light from one pixel (scintillator segment 2) to pixels adjacent to the one pixel through the adhesive layer 5 to cause crosstalk, which is not desirable. The thickness of the adhesive layer 5 can be measured from an observed image obtained by observing a cross-section in a thickness direction using an electron microscope or an optical microscope. Since the reflective layer 4 and the adhesive layer 5 form a polymer network structure in each layer, an interface between these layers is clear. When a pigment concentration is different, it is even clearer, making it easier to determine the thickness.

A conventional scintillator array used in an X-ray CT scanner and the like requires that light generated by X-rays be confined within pixels and efficiently extracted to a photodiode side. Since alignment accuracy is required when bonding the scintillator array to the photodiode, it is necessary that a pitch between pixels does not fluctuate easily with temperature and that the warpage of the scintillator itself is particularly small. When the warpage of the scintillator is large, the thickness of the adhesive layer that fills a space between the scintillator array and the photodiode when bonded to the photodiode will be uneven, and where the adhesive layer is thick, the light will enter adjacent pixels, increasing crosstalk, which will result in uneven X-ray detection sensitivity. Further, the X-ray detection sensitivity decreases because air bubbles can easily enter the adhesive layer, which scatters light from the scintillator.

On the other hand, a known technology controls the number of reflective particles per unit area (5 μm×5 μm) and a ratio of aggregates of reflective particles per unit area (10 μm×10 μm) in the reflective layer between scintillator segments to equalize a shrinkage ratio of the reflective layer portion when the light transmissive resin solidifies, thereby preventing the warpage of the scintillator array during and after manufacturing.

A known scintillator array has the glass transition point of a light transmissive resin constituting the reflective layer of 50° C. or more, and the thermal expansion coefficient of the light transmissive resin at a temperature higher than the glass transition point of $3.5 \times 10^{-5}/°$ C. or less. In general, the thermal expansion coefficient of the light transmissive resin changes significantly after the glass transition point, and the warpage caused by this change is adjusted by setting conditions.

Further, a known scintillator array has a constitution that the scintillator segments are integrated by the reflective layer, the glass transition point of the light transmissive resin of the reflective layer is 50° C. or more, and the glass transition point of the light transmissive resin of a second reflective layer disposed on an X-ray incident surface side of the scintillator segments is 30° C. or less to reduce the warpage of the scintillator array.

Although the warpage of these scintillators can be improved to some extent, the scintillator array must be made finer to meet a demand for improved image quality, and measures must be taken to prevent image degradation due to crosstalk and lowering of detection sensitivity caused by the warpage.

The scintillator array of the embodiment includes a first reflective layer that forms the structure 20 together with the scintillator segments and a second reflective layer disposed on an X-ray incident surface side of the scintillator segments.

In the scintillator array of the embodiment, the second reflective layer can be formed by a method of bonding a pre-formed light-reflecting film to the structure via an adhesive layer instead of a method of applying a slurry where the reflective particles are dispersed in the light transmissive resin to the X-ray incident surface side of the scintillator array and thermally curing the slurry. The scintillator array with such a constitution is easier to fabricate than conventional ones. Furthermore, the warpage can be reduced by controlling the thickness of the adhesive layer within a certain range.

Next, an example of a manufacturing method of the scintillator array 1 will be explained. The scintillator array 1 is manufactured, for example, as follows. First, reflective particles and a resin composition in an uncured state that constitutes a light transmissive resin (uncured material of the light transmissive resin) are prepared, and these are mixed to prepare a mixture. Next, a scintillator segments 2 processed into a predetermined shape are placed at regular intervals. The mixture of the reflective particles and the resin composition in the uncured state described above is applied or filled between the adjacent scintillator segments 2.

The resin composition in the uncured state preferably has a viscosity of 0.2 Pa·s or more and 1.0 Pa·s or less (200 cps or more and 1000 cps or less). When the viscosity of the resin composition is larger than 1.0 Pa·s, flowability becomes poor and workability of applying or filling the resin composition between the scintillator segments 2 decreases. When the viscosity of the resin composition is less than 0.2 Pa·s, the flowability becomes too high, resulting in lowering of applying performance or filling performance. Further, total light transmittance of the light transmissive resin is preferably 85% or more. When the total light transmittance of the light transmissive resin is less than 85%, the reflection efficiency of the reflective layer 3 becomes more likely to decrease.

The mixture of the reflective particles and the resin composition in the uncured state is applied or filled between the scintillator segments 2 and then the resin composition in the mixture is cured to form the reflective layer 3, thereby adjacent scintillator segments 2 are bonded and integrated to form the structure 20. The curing processing of the mixture is appropriately set according to types or the like of the resin composition in the uncured state and a curing agent. For example, in the case of a thermosetting resin composition, a curing reaction is promoted by performing heat treatment.

Next, the reflective layer 4 is formed above the surface 20a of the structure 20 via the adhesive layer 5. To manufacture the white film, a resin containing reflective particles that can be used to form the reflective layer 3 is processed into a sheet form using a doctor blade or the like and cured. Not limited to this, a commercially available white film may also be used. Such a commercially available white film is formed by kneading reflective particles such as titanium oxide, alumina, silica, and the like, into a light transmissive resin such as epoxy resin or polyester resin and processing it into a sheet form. A thickness of the white film is, for example, 50 μm or more and 250 μm or less.

A light transmissive resin with a viscosity of 0.2 Pa·s or more and 1.0 Pa·s or less is applied to the surface 20a of the structure 20 as the adhesive layer 5, a white film with a predetermined size is placed thereon, and the resultant is cured under pressure. Curing under pressure is a process made possible by the use of the white film for the reflective layer 4, which is difficult to achieve with conventional processes. Therefore, the process is also considered to contribute to the reduction of the warpage.

(Radiation Detector)

Figure 4:
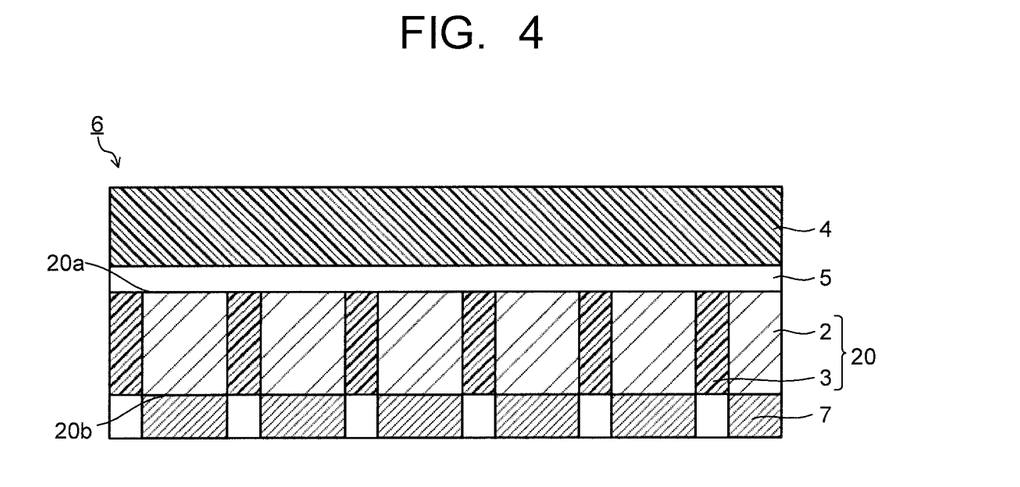
FIG. 4 is a view illustrating a constitutional example of a radiation detector.

A radiation detector of an embodiment includes the scintillator array 1 as a fluorescence generator that emits light according to incident radiation rays and further includes a photoelectric converter that receives light from the fluorescence generator and converts light output to electric output. FIG. 4 is a view illustrating a constitutional example of the radiation detector and illustrates an X-ray detector. An X-ray detector 6 illustrated in FIG. 4 includes the scintillator array 1 as the fluorescence generator and photoelectric conversion elements 7 as the photoelectric converter.

The X-ray detector 6 includes the photoelectric conversion elements 7 that are integrally provided on the surface 20b of the structure 20. The photoelectric conversion elements 7 detect light (visible light) formed by converting X-rays at the scintillator segments 2. Examples of the photoelectric conversion element 7 include a photodiode. The photoelectric conversion elements 7 are arranged to correspond to the scintillator segments 2, respectively. These components constitute the radiation detector.

(Radiation Inspection Device)

A radiation inspection device of the embodiment includes a radiation source that emits radiation rays toward an inspection target, and a radiation detector that detects the radiation rays transmitted through the inspection target. For the radiation detector, the radiation detector of the embodiment can be used.

Figure 5:
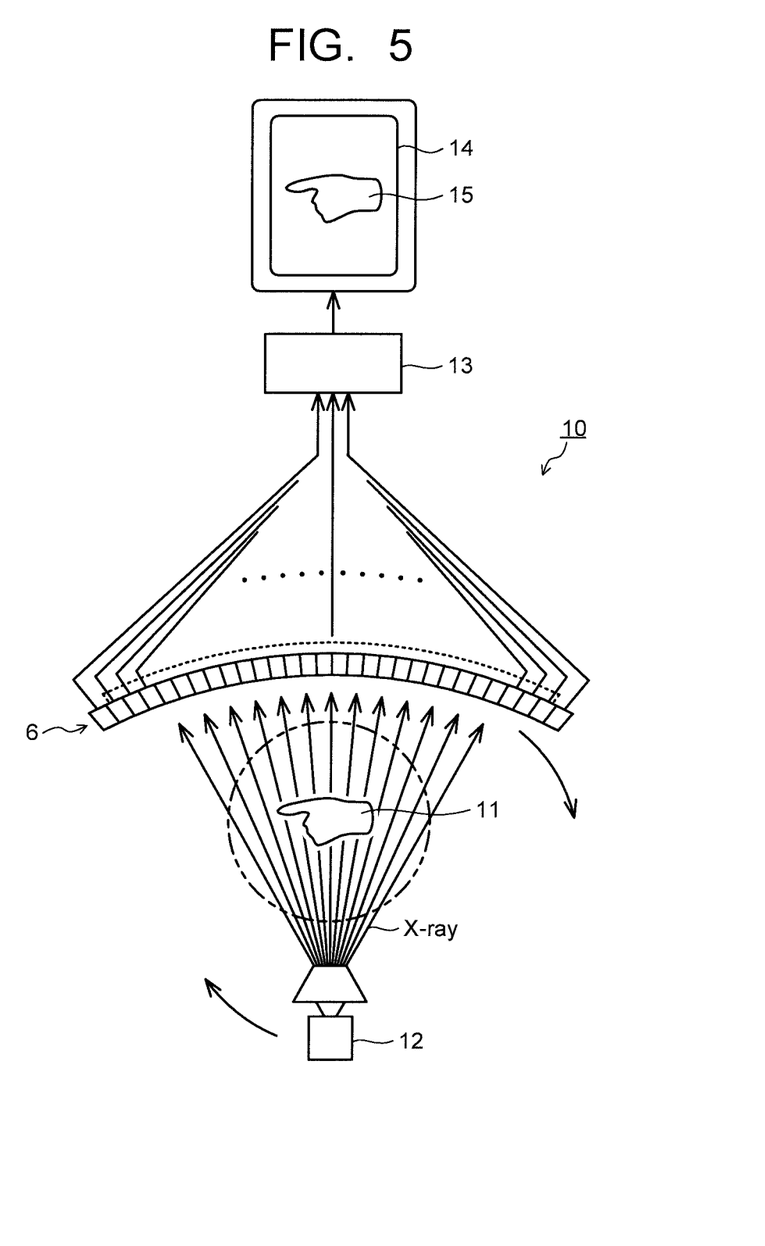
FIG. 5 is a view illustrating a constitutional example of a radiation inspection device.

FIG. 5 is a view illustrating a constitutional example of the radiation inspection device. FIG. 5 illustrates an X-ray CT scanner 10, a specimen 11, an X-ray tube 12, a computer 13, a display 14, and a specimen image 15. The X-ray CT scanner 10 includes the X-ray detector 6. The X-ray detector 6 is attached to, for example, an inner wall surface of a cylinder where an imaging portion of the specimen 11 is arranged. At an almost center of an arc of the cylinder where the X-ray detector 6 is attached, the X-ray tube 12 that emits X-rays is placed. The specimen 11 is arranged between the X-ray detector 6 and the X-ray tube 12. On an X-ray incident surface side of the X-ray detector 6, a not-illustrated collimator is provided.

The X-ray detector 6 and the X-ray tube 12 are configured to rotate around the specimen 11 while photographing with the X-rays. Image information of the specimen 11 is three-dimensionally collected from different angles. Signals obtained by X-ray photography (electric signals converted by the photoelectric conversion elements) are processed by the computer 13 and displayed on the display 14 as the specimen image 15. The specimen image 15 is, for example, a tomogram of the specimen 11. Using the scintillator array 1 in which the scintillator segments 2 are two-dimensionally arranged as illustrated in FIG. 1 also can constitute a multi-tomogram type X-ray CT scanner 10. In this case, a plurality of tomograms of the specimen 11 are photographed at the same time and, for example, a photographed result can be three-dimensionally drawn.

The X-ray CT scanner 10 illustrated in FIG. 5 includes the X-ray detector 6 including the scintillator array 1. As described above, the scintillator array 1 has excellent light output because the reflection efficiency of visible light emitted from the scintillator segments 2 is high based on the constitution of the reflective layer 3, the reflective layer 4, and the like. Using the X-ray detector 6 including the scintillator array 1 can shorten the photographing time by the X-ray CT scanner 10. This can shorten exposure time of the specimen 11 and achieve low radiation exposure. The radiation inspection device (X-ray CT scanner 10) is applicable not only to the X-ray inspection for medical diagnosis of a human body but also to the X-ray inspection for animals, the X-ray inspection for industrial usage, and so on.

Further, the radiation inspection device also contributes to an improvement in inspection accuracy by an X-ray nondestructive inspection device.

EXAMPLES

Concrete examples of the scintillator array 1 and their evaluation results are described. In the examples and comparative examples, the structure 20 with the scintillator segments 2 and reflective layer 3 before forming the reflective layer 4 on the X-ray incident surface was fabricated as follows.

Phosphor powder having a composition of $Gd_2O_2S:Pr$ (Pr concentration=0.05 mol %) was temporarily molded by rubber pressing, and the temporarily molded body was degassed and sealed in a capsule made of tantalum (Ta) and then set in a hot isostatic pressing (HIP) device. The HIP device was filled with argon gas as a pressurizing medium, and the process was carried out for 3 hours under conditions of a pressure of 147 MPa and a temperature of 1425° C. In the above manner, a sintered compact in a cylindrical shape having a diameter of approximately 80 mm×a height of approximately 120 mm was fabricated. From the sintered compact, scintillator segments 2 each with 0.8 mm in length×0.7 mm in width×0.7 mm in thickness were cut in a matrix form of 84 segments in a length direction and 31 segments in a width direction. Next, the structure 20 was fabricated by integrating the scintillator segments 2 through the reflective layer 3 made of the mixture of 65% reflective particles and 35% light transmissive resin by mass ratio. The reflective layer 3 with a thickness of 0.1 mm was arranged in vertical and horizontal directions of the structure 20, respectively. For the reflective particles, a mixture of 80% titanium oxide particles and 20% alumina particles by mass ratio was used. The structure 20 with 76 mm in length, 25 mm in width, and 0.7 mm in thickness was thereby fabricated.

Example 1

The adhesive layer 5 was formed on the surface 20a of the fabricated structure 20 by applying an adhesive containing titanium oxide and epoxy resin (glass transition point after curing: 85° C.) with a thickness of 10 μm. A white PET film (manufactured by Mitsubishi Chemical, thickness: 100 μm) as the reflective layer 4 was placed on the adhesive layer 5, and the scintillator array 1 was completed by curing the resultant at the room temperature for 24 hours while applying a load of 16 kg. After the load was removed, the warpage was measured to be 15 μm. The result is listed in Table 1.

Example 2

The adhesive layer 5 was formed on the surface 20a of the fabricated structure 20 by applying an adhesive containing titanium oxide and epoxy resin (glass transition point after curing: 85° C.) with a thickness of 15 μm. A white PET film (manufactured by Mitsubishi Chemical, thickness: 100 μm) as the reflective layer 4 was placed on the adhesive layer 5, and the scintillator array 1 was completed by curing the resultant at the room temperature for 24 hours while applying a load of 10 kg. After the load was removed, the warpage was measured to be 20 μm. The result is listed in Table 1.

Example 3

A white PET film (manufactured by Mitsubishi Chemical, thickness: 100 μm) as the reflective layer 4 was bonded to the surface 20a of the fabricated structure 20 via a prepreg epoxy adhesive sheet (thickness: 25 μm) as the adhesive layer 5. When the bonding, the structure 20, the epoxy adhesive sheet, and the white PET film were placed on top of each other, a load of 16 kg was applied, and these were adhered by heating at the temperature of 100° C. The load was removed after cooling the laminate to the room temperature, and the scintillator array 1 was completed. The warpage was measured to be 20 μm. The result is listed in Table 1.

Example 4

A mixture of 65% titanium oxide particles and 35% epoxy resin (glass transition point after curing: 55° C.) by mass ratio was formed into a form of a fluorocarbon resin sheet using a doctor blade and cured at the room temperature for 24 hours to form a white film. A thickness of the obtained white film was 150 μm. Next, the white film as the reflective layer 4 was arranged above the surface 20a of the fabricated structure 20 via a prepreg epoxy adhesive sheet (thickness: 25 μm) as the adhesive layer 5. A load of 20 kg was applied and the resultant was heated at the temperature of 100° C. for adhesion. The load was removed after cooling the laminate to the room temperature, and the scintillator array 1 was completed. The warpage was measured to be 30 μm. The result is listed in Table 1.

Example 5

A mixture of 65% titanium oxide particles and 35% epoxy resin (glass transition point after curing: 55° C.) by mass ratio was formed into a form of a fluorocarbon resin sheet using a doctor blade and cured at the room temperature for 24 hours to form a white film. A thickness of the obtained white film was 120 μm. Next, the white film was arranged above the surface 20a of the fabricated structure 20 via a prepreg epoxy adhesive sheet (thickness: 25 μm) as the adhesive layer 5. A load of 20 kg was applied and the resultant was heated at the temperature of 100° C. for adhesion. The load was removed after cooling the laminate to the room temperature, and the scintillator array 1 was completed. The warpage was measured to be 25 μm. The result is listed in Table 1.

Comparative Example 1

A mixture of titanium oxide and epoxy resin (glass transition point after curing: 85° C.) was applied on the surface 20a of the fabricated structure 20, and cured at the temperature of 100° C. for three hours. The reflective layer 4 was formed by polishing after curing to make the thickness to be 150 μm. Since the resin is hard at the room temperature, internal stress generated in the epoxy resin during the curing process was large, and the warpage was measured to be 140 μm. The result is listed in Table 1.

Comparative Example 2

A mixture of titanium oxide and epoxy resin (glass transition point after curing: 85° C.) was applied on the surface 20a of the fabricated structure 20 and cured at the temperature of 100° C. for three hours. The reflective layer 4 was formed by polishing after curing to make the thickness to be 130 μm. Compared to Comparative Example 1, the thickness of the reflective layer 4 was thinner, which relaxed the stress, and the warpage was measured to be 132 μm. The result is listed in Table 1.

Comparative Example 3

A solution of titanium oxide and nitrocellulose dispersed in a solvent was sprayed and the solvent was evaporated by heating to form a coating film that became the reflective layer 4 on the surface 20a of the fabricated structure 20. The thickness of the coating film after drying was 100 μm. As a result of drying and shrinking, the warpage was measured to be 100 μm. The result is listed in Table 1.

TABLE 1

|  | Warpage | Correction of warpage |
| --- | --- | --- |
| Example 1 | 15 μm | Unnecessary |
| Example 2 | 20 μm | Unnecessary |
| Example 3 | 20 μm | Unnecessary |
| Example 4 | 30 μm | Unnecessary |
| Example 5 | 25 μm | Unnecessary |
| Comparative Example 1 | 140 μm | Necessary |
| Comparative Example 2 | 132 μm | Necessary |
| Comparative Example 3 | 100 μm | Necessary |

In the comparative examples, the same light transmissive resin as in the examples is applied onto the X-ray incident surface, but because the reflective layer after curing is thick, the internal stress generated during curing is large, resulting in significant warpage. In the examples, the stress during curing can be reduced by using the white film and making the adhesive layer thin, and the warpage can be greatly reduced. In the examples, correction of the warpage was not necessary, but in the comparative examples, further heat treatment and polishing are required to correct the warpage, and because the scintillator array 1 is greatly warped, the thicknesses of the reflective layer 4 on the X-ray incident surface and the scintillator segments 2 became non-uniform in a plane, which tended to cause variations in output characteristics.

According to the scintillator array of the embodiment, the warpage can be greatly reduced and the thickness of the adhering surface with the photoelectric conversion elements can be made uniform, thus reducing the variation in the output characteristics. It also reduces the need for heat treatment, polishing, and other processes to correct the warpage, which is an extremely significant industrial advantage.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes may be made without departing from the spirit of the inventions. The embodiments and modifications would fall within the scope and spirit of the inventions and fall within the inventions as set forth in accompanying claims and their equivalents.

What is claimed is:

1. A scintillator array comprising:
 a structure comprising at least one scintillator segment and a first reflective layer, the at least one scintillator segment and the first reflective layer having a first surface and a second surface, the at least one scintillator segment having a sintered compact containing a rare earth oxysulfide phosphor, and the first reflective layer being configured to reflect light; and a second reflective layer provided above the first surface via an adhesive layer, the adhesive layer having a thickness of 2 μm or more and 40 μm or less, and the second reflective layer having a film configured to reflect light.

2. The scintillator array according to claim 1, wherein the thickness of the adhesive layer is 5 μm or more and 30 μm or less.

3. The scintillator array according to claim 1, wherein at least one reflective layer selected from the group consisting of the first and second reflective layers, contains:

a resin having at least one selected from the group consisting of epoxy resin, silicone resin, phenol resin, urea resin, melamine resin, polyester resin, polyurethane resin, and acrylic resin; and reflective particles having at least one selected from the group consisting of titanium oxide, aluminum oxide, silicon oxide, barium sulfate, zinc oxide, zirconium oxide, and gadolinium oxide, the reflective particles being configured to reflect light.

4. The scintillator array according to claim 3, wherein the resin in the at least one reflective layer has a first mass ratio of 15% or more and 60% or less, the reflective particles in the at least one reflective layer have a second mass ratio of 40% or more and 85% or less, and the sum of the first mass ratio and the second mass ratio is 100%.

5. The scintillator array according to claim 1, wherein the adhesive layer contains at least one resin selected from the group consisting of epoxy resin, silicone resin, acrylic resin, urethane resin, polyester resin, and polyolefin resin, the at least one resin being cured by light, heat, or moisture.

6. The scintillator array according to claim 5, wherein the adhesive layer further contains at least one selected from the group consisting of titanium oxide, zirconium oxide, aluminum oxide, and silicon oxide.

7. The scintillator array according to claim 1, wherein the rare earth oxysulfide phosphor has a composition represented by a general formula $RE_2O_2S:Pr$ where in the general formula, RE denotes at least one element selected from the group consisting of Y, Gd, La and Lu, and a content of Pr to a content of $RE_2O_2S$ is 0.001 mol % or more and 10 mol % or less.

8. A radiation detector comprising the scintillator array according to claim 1.

9. A radiation inspection device comprising the radiation detector according to claim 8.

10. A method for manufacturing a scintillator array, comprising:

forming a structure comprising at least one scintillator segment and a first reflective layer, the at least one scintillator segment and the first reflective layer having a first surface and a second surface, the at least one scintillator segment having a sintered compact containing a rare earth oxysulfide phosphor, and the first reflective layer being configured to reflect light; and forming a second reflective layer above the first surface via an adhesive layer having a thickness of 2 μm or more and 40 μm or less, the second reflective layer having a film configured to reflect light.

* * * * *